United States Patent
Hoffmann et al.

(10) Patent No.: US 8,178,583 B2
(45) Date of Patent: May 15, 2012

(54) COMPOUNDS

(75) Inventors: Torsten Hoffmann, Weil am Rhein (DE); Holger Kuehne, Loerrach (DE); Eric J. Niesor, Nyon (CH); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 92 days.

(21) Appl. No.: 12/631,884

(22) Filed: Dec. 7, 2009

(65) Prior Publication Data

US 2010/0160441 A1 Jun. 24, 2010

(30) Foreign Application Priority Data

Dec. 19, 2008 (EP) .................................. 08172381

(51) Int. Cl.
*A61K 31/13* (2006.01)
*C07C 211/33* (2006.01)
(52) U.S. Cl. ...................... 514/579; 564/462
(58) Field of Classification Search .............. 564/462; 514/579

See application file for complete search history.

(56) References Cited

U.S. PATENT DOCUMENTS

| 6,426,365 | B1 | 7/2002 | Shinkai et al. |
| 7,375,119 | B2 * | 5/2008 | Kawaguchi et al. ........... 514/340 |
| 7,435,823 | B2 * | 10/2008 | Potashman et al. ........... 546/153 |

FOREIGN PATENT DOCUMENTS

EP 1 020 439 7/2000

OTHER PUBLICATIONS

Shinkai, H. et al, Jour. of Medicinal Chemistry 43: 356-3572 (2000) XP002416562.
Maeda, K. et al, Bioorganic & Medicinal Chemistry Letters, 14:10 92004) 2589-2591 XP004841246.
Okamoto et al., Nature, 406, pp. 203-207 (2000).

* cited by examiner

*Primary Examiner* — Golam M M Shameem
(74) *Attorney, Agent, or Firm* — George W. Johnston; Patricia S. Rocha-Tramaloni; Gene J. Yao

(57) ABSTRACT

The invention is concerned with compounds of formula I:

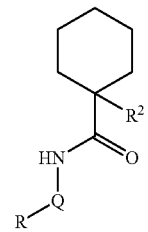

wherein R, $R^2$, and Q are as defined in the description and in the claims, as well as physiologically acceptable salts thereof. These compounds are useful as inhibitors of cholesteryl ester transfer protein (CETP).

20 Claims, No Drawings

COMPOUNDS

PRIORITY TO RELATED APPLICATION(S)

This application claims the benefit of European Patent Application No. 08172381.9, filed Dec. 19, 2008, which is hereby incorporated by reference in its entirety.

BACKGROUND OF THE INVENTION

Cholesteryl ester transfer protein (CETP) facilitates the transport of cholesteryl esters and triglycerides between lipoproteins. The inhibition of CETP has resulted in higher HDL levels and therefore is believed to be a treatment for cardiovascular diseases such as atherosclerosis.

SUMMARY OF THE INVENTION

The present invention relates to novel compounds useful as inhibitors of cholesteryl ester transfer protein (CETP), compositions comprising the novel compounds, and the use thereof.

DETAILED DESCRIPTION OF THE INVENTION

In a first embodiment the present invention provides a compound of formula I:

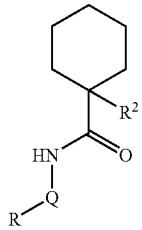

I and pharmaceutically acceptable salts thereof, wherein:
R is selected from the group consisting of:
(1) —$SR^1$ wherein $R^1$ is hydrogen or a $C(O)C_1$-$C_{10}$alkyl; and
(2) a group of formula II:

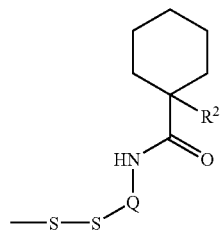

II $R^2$ is a $C_1$-$C_{10}$alkyl;
Q is selected from the group consisting of:
(1) a group of formula IIa:

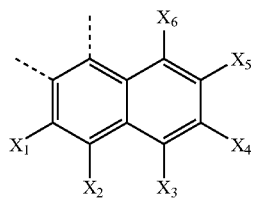

(2) a group of formula IIb:

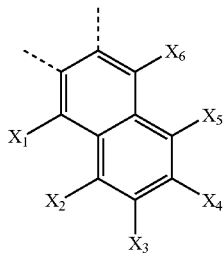

(3) a group of formula IIc:

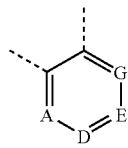

(4) a group of formula IId:

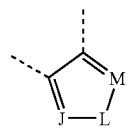

(5) a group of formula IIe:

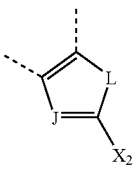

wherein $X_1$, $X_2$, $X_3$, $X_4$, $X_5$ and $X_6$ are independently selected from the group consisting of hydrogen, $C_1$-$C_6$alkyl, $C_3$-$C_8$cycloalkyl, halo-$C_1$-$C_6$alkyl, halo-$C_3$-$C_8$ cycloalkyl, halo-$C_1$-$C_6$alkoxy, halogen, cyano, nitro, acyl and aryl;
A is C—$X_1$ or N;
D is C—$X_2$ or N;
E is C—$X_3$ or N;
G is C—$X_4$ or N;
J is C—$X_1$ or N;
L is S, O or NH; and
M is C—$X_2$ or N;
wherein in formula IIc at least one of A, D, E and G is N.
Examples of a $C_1$-$C_{10}$alkyl include branched and straight-chain monovalent saturated aliphatic hydrocarbon radicals of one to ten carbon atoms, e.g. methyl, ethyl, propyl, isopropyl, butyl, isobutyl, tert.-butyl, the isomeric pentyls, the isomeric hexyls, the isomeric heptyls, the isomeric octyls, the isomeric nonyls and the isomeric decyls.
Examples of a halogen include fluoro, chloro, bromo and iodo.
Examples of a halo-$C_1$-$C_6$alkyl include $C_1$-$C_6$alkyl groups as defined above wherein at least one of the hydrogen atoms of the $C_1$-$C_6$alkyl group is replaced by a halogen atom, e.g.

fluoro or chloro, e.g. trifluoromethyl, difluoromethyl, fluoromethyl, 1,2,2,2-tetrafluoro-1-trifluoromethyl-ethyl, pentafluoroethyl and chlorodifluoromethyl.

Examples of a halo-$C_1$-$C_6$alkoxy include alkoxy groups of formula O—$C_1$-$C_6$alkyl wherein at least one of the hydrogen atoms of the alkoxy group is replaced by a halogen atom, e.g. fluoro or chloro, e.g. trifluoromethoxy, difluoromethoxy, fluoromethoxy and chlorodifluoromethoxy.

Examples of a $C_3$-$C_8$cycloalkyl include saturated carbocyclic groups containing from 3 to 8 carbon atoms, such as cyclopropyl, cyclobutyl, cyclopentyl, cyclohexyl, cycloheptyl and cyclooctyl. Examples of a halo-$C_3$-$C_8$cycloalkyl include 1-fluorocyclobutyl.

Examples of pharmaceutically acceptable salts include: (1) acid addition salts, formed with inorganic acids such as hydrochloric acid, hydrobromic acid, sulfuric acid, nitric acid, phos-phoric acid, and the like; or formed with organic acids such as acetic acid, propionic acid, hexan-oic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulf-onic acid, 1,2-ethane-dis-ulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methyl-glucamine, and the like.

"Pharmaceutically acceptable carriers" are intended to include any and all material compatible with pharmaceutical administration including solvents, dispersion media, coatings, antibacterial and antifungal agents, isotonic and absorption delaying agents, and other materials and compounds compatible with pharmaceutical administration.

Unless otherwise indicated, the term "a compound of the formula" or "a compound of formula" or "compounds of the formula" or "compounds of formula" refers to any compound selected from the genus of compounds as defined by the formula.

In one embodiment, the present invention provides a compound of formula I wherein $R^2$ is a $C_1$-$C_6$alkyl. In another embodiment, the present invention provides a compound of formula I wherein $R^2$ is 2-ethyl-but-1-yl.

In one embodiment, the present invention provides a compound of formula I wherein R is a group of formula II, wherein both groups Q are identical.

In one embodiment, the present invention provides a compound of formula I wherein Q is of formula IIa or IIb.

In one embodiment, the present invention provides a compound of formula I wherein R is —$SR^1$ wherein $R^1$ is hydrogen or $C(O)C_1$-$C_{10}$alkyl.

In general, the nomenclature used in this Application is based on AUTONOM™ v.4.0, a Beilstein Institute computerized system for the generation of IUPAC systematic nomenclature.

EXAMPLE 1

Preparation of thioisobutyric acid S-(3-{[1-(2-ethyl-butyl)-cyclohexanecarbonyl]-amino}-naphthalen-2-yl)ester

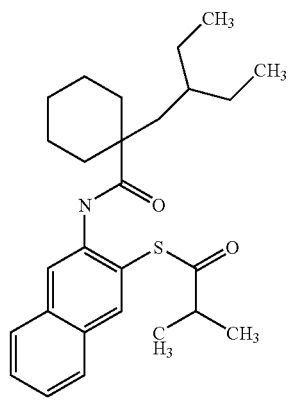

A) To a solution of 3-amino-naphthalene-2-thiol in pyridine are added two mol equivalents of 1-(2-ethyl-butyl)-cyclohexanecarbonyl chloride at room temperature. After completion of the addition, the reaction mixture is heated to 60° C. for 2 hours. The pyridine is then removed under reduced pressure, water is added and the mixture is extracted with ethyl acetate. The combined extracts are washed with sat. $NaHCO_3$-solution, diluted hydrochloric acid and brine, dried ($Na_2SO_4$) and concentrated to obtain crude 1-(2-ethyl-butyl)-cyclohexanecarbothioic acid S-(3-{[1-(2-ethyl-butyl)-cyclohexanecarbonyl]-amino}-naphthalen-2-yl)ester.

B) The crude product obtained in step A) is dissolved in a mixture of methanol and tetra-hydrofuran (1:1). Then 3.5 mol equivalents of potassium hydroxide are added at room temperature and the mixture is stirred for 1 hour. Then water is added and the mixture is washed with n-hexane. The aqueous layer is then acidified by addition of $KHSO_4$ and extracted with chloroform. The combined extracts are washed with water and brine, dried ($Na_2SO_4$) and concentrated to obtain 1-(2-ethyl-butyl)-cyclohexanecarboxylic acid (3-mercapto-naphthalen-2-yl)-amide.

C) To a chloroform solution of the product obtained in step B) are added 1.05 mol equivalents of isobutyryl chloride and 2.5 mol equivalents of pyridine at room temperature. The mixture is stirred for 1 hour, concentrated and then n-hexane is added. The solids are filtered off and the filtrate is concentrated. The remaining residue is purified by silica gel column chromatography to obtain the desired title compound.

EXAMPLE 2

Preparation of 1-methyl-cyclohexanecarboxylic acid(2-mercapto-naphthalen-1-yl)-amide

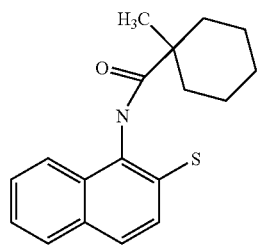

A) To a solution of 1-amino-naphthalene-2-thiol in pyridine are added two mol equivalents of 1-methyl-cyclohexanecarbonyl chloride at room temperature. After completion of the addition, the reaction mixture is heated to 60° C. for 2 hours. The pyridine is then removed under reduced pressure, water is added and the mixture is extracted with ethyl acetate. The combined extracts are washed with sat. $NaHCO_3$-solution, diluted hydrochloric acid and brine, dried ($Na_2SO_4$) and concentrated to obtain crude 1-methyl-cyclohexanecarbothioic acid S-{1-[(1-methyl-cyclohexanecarbonyl)-amino]-naphthalen-2-yl}ester.

B) The crude product obtained in step A) is dissolved in a mixture of methanol and tetra-hydrofuran (1:1). Then 3.5 mol equivalents of potassium hydroxide are added at room temperature and the mixture is stirred for 1 hour. Then water is added and the mixture is washed with n-hexane. The aqueous layer is then acidified by addition of $KHSO_4$ and extracted with chloroform. The combined extracts are washed with water and brine, dried ($Na_2SO_4$) and concentrated to obtain the desired title compound.

C) The compounds of formula I are cholesteryl ester transfer protein (CETP) inhibitors. Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are three different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. Therefore, by inhibiting CETP activity there is the potential to inverse this relationship towards a lower risk and ultimately to protect against coronary heart diseases and associated mortality.

Thus, CETP inhibitors are useful as medicaments for the treatment and/or prophylaxis of atherosclerosis, peripheral vascular disease, dyslipidemia, hyperbeta-lipoproteinemia, hypoalphalipoproteinemia, hypercholesterolemia, hypertriglyceridemia, familial hyper-cholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

As described above, the compounds of formula I of the present invention can be used as medicaments for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as a medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutically active substances for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hyper-cholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or pro-phylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

The invention further relates to the use of compounds of formula I as defined above for the treatment and/or prophylaxis of diseases that are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts possess valuable pharmacological properties. Specifically, it has been found that the compounds of the present invention are inhibitors of the cholesteryl ester transfer protein (CETP).

The following tests can be carried out in order to determine the activity of the compounds of formula I.

Activity of CETP inhibitors is determined using a buffer assay system. Partially purified CETP transfers radiolabeled cholesteryl ester from HDL donor particles to biotin-labeled LDL acceptor particles. The reaction is stopped by addition of streptavidin-coupled scintillation proximity assay (SPA) beads. These beads capture the biotinylated acceptor particles and transferred radioactivity is measured. The assay system can be purchased and performed according to manufacturer's recommendations (Amersham Biosciences). Inhibitory activity of compounds can be determined as percentage of positive control activity containing CETP together with donor and acceptor particles. Serial dilution of compounds is performed in order to determine the $IC_{50}$ values.

Activity of the compounds is subsequently measured in the presence of plasma using the same assay as described above except that the source of CETP was human lipoprotein-deprived serum (LPDS). Inhibitory activity of compounds is determined as percentage of positive control activity containing all the assay components except compound. Serial dilution of compounds is performed in order to determine the $IC_{50}$ values.

In vivo activity of the compounds of formula I is determined in hamster using the following protocol:

Male golden Syrian hamsters (6-week-old, 100-130 g) under standard chow diet receive compounds in the morning by oral gavage using appropriate vehicle, blood is taken 2 h later by retro-orbital bleeding under isofluran anesthesia and 7 h later on sacrificed animals. Plasma is separated from blood using low speed centrifugation and CETP activity is measured in plasma using the radioactive CETP activity assay as described above except that diluted plasma replaced LPDS. In vivo CETP inhibition is expressed as CETP activity remaining in the plasma of treated animals as compared to plasma CETP activity of placebo treated animals.

Efficacy of compounds in modulating plasma lipid levels can be determined in hamsters after 7 days of daily administration of compounds. Male hamsters are acclimated for 3-4 days to receive food as a paste made of 10 g chow and 10 g water per day. Compounds are then mixed within this paste and a portion containing the proper amount of compounds is given every morning for 7 days. Alternatively compounds can be given by oral gavage using the proper vehicle. Blood is taken before compound treatment by retro-orbital bleeding and at the end of the treatment on sacrificed animals. Plasma is separated from blood by low speed centrifugation and selected organs are taken (e.g liver, fat, brain, etc.). Effects of compounds on plasma lipid levels are determined by measuring total cholesterol, HDL-cholesterol, LDL-cholesterol and triglyceride using colorimetric enzymatic assays (Roche Diagnostic GmbH, Mannheim, Germany). HDL-C, LDL-C and VLDL-C are e.g., quantified using size exclusion chromatography on superpose-6 column using SMART™ system (Pharmacia). Lipoprotein distribution is calculated assuming a Gaussian distribution for each peak, using a non-linear, least-squares curve-fitting procedure to calculate the area under the curve. Plasma samples are also used to quantify CETP activity as described above. Compound concentration is also determined in plasma and selected tissues as liver, fat, heart, muscle and brain.

Efficacy of compounds in modulating plasma lipid levels is also determined in cholesterol/fat fed hamsters. The protocol is identical as described above except that animals are fed with chow diet enriched with 10% (w/w) saturated fat and 0.05% (w/w) cholesterol. Animals receive this high fat diet 2 weeks before starting compound administration and continue this diet throughout the study. The 2 weeks pre-treatment induces an increase in plasma cholesterol and triglyceride levels allowing a better assessment of LDL-C and triglyceride lowering.

Efficacy of compounds in its ability to acutely raise HDL-C can be assessed in cynomolgus monkeys. Animals are fed with standard primate maintenance diet. Compounds are formulated with appropriate vehicle and administered to animals by oral gavage. Blood is taken before and at several time-points after compound administration (usually 30 min, 1 h, 2 h, 4 h, 7 h and 24 h). Plasma is separated from blood by low speed centrifugation and CETP activity and plasma lipids are quantified. Compound potency and efficacy can be assessed by measuring the HDL-C increase after this single-dose administration. In such a pharmacodynamic model the extent together with the kinetics of the pharmacologic effect can be assessed.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable salts, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragées and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, e.g., 0.5-100 mg, of a compound of formula I.

The following examples serve to illustrate the present invention in more detail. They are, however, not intended to limit its scope in any manner.

EXAMPLE A

Film Coated Tablets

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

EXAMPLE B

Capsules

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection Solutions

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

EXAMPLE D

Soft Gelatin Capsules

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

The invention claimed is:

1. A compound of formula I:

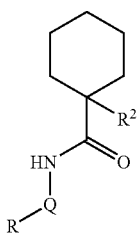

or a pharmaceutically acceptable salt thereof, wherein:
R is selected from the group consisting of:
  (1) —SR$_1$ wherein R$^1$ is hydrogen or a C(O)C$_1$-C$_{10}$alkyl; and
  (2) a group of formula II:

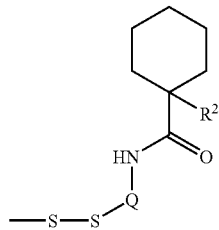

R$^2$ is a C$_1$-C$_{10}$alkyl; and
Q is selected from the group consisting of:
  (1) a group of formula IIa:

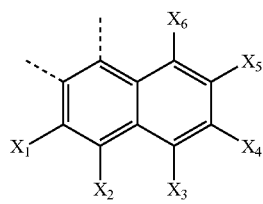

(2) a group of formula IIb:

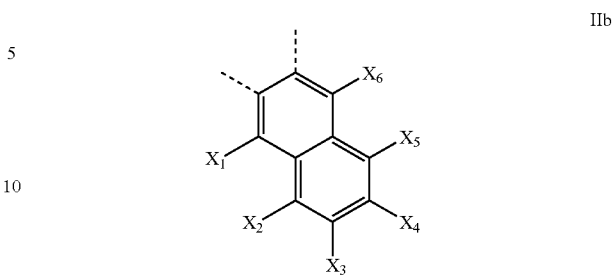

wherein X$_1$, X$_2$, X$_3$, X$_4$, X$_5$ and X$_6$ are independently selected from the group consisting of hydrogen, C$_1$-C$_6$alkyl, C$_3$-C$_8$cycloalkyl, halo-C$_1$-C$_6$alkyl, halo-C$_3$-C$_8$cycloalkyl, halo-C$_1$-C$_6$alkoxy, halogen, cyano, nitro, acyl and aryl.

2. A compound according to claim 1, wherein Q is of formula IIa:

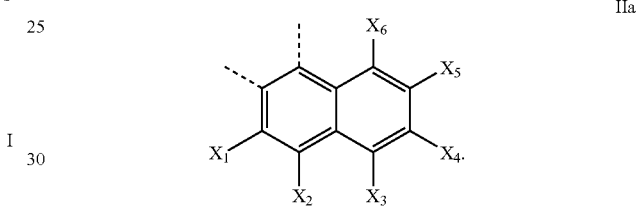

3. A compound according to claim 1, wherein Q is of formula IIb:

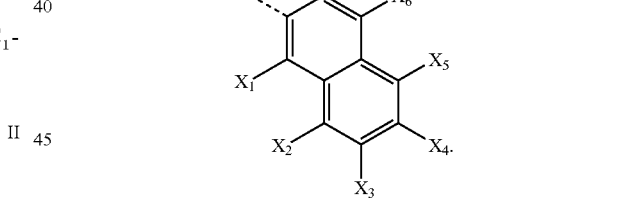

4. A compound according to claim 1, wherein R$^2$ is a C$_1$-C$_6$alkyl.

5. A compound according to claim 1, wherein R$^2$ is 2-ethyl-but-1-yl.

6. A compound according to claim 1, wherein R is a group of formula II, and wherein both groups Q are identical.

7. A compound according to claim 1, wherein R is —SR$^1$ and wherein R$^1$ is hydrogen.

8. A compound according to claim 1, wherein R is —SR$^1$ and wherein R$^1$ is C(O)C$_1$-C$_{10}$alkyl.

9. A compound according to claim 1, wherein X$_1$, X$_2$, X$_3$, X$_4$, X$_5$ and X$_6$ are hydrogen.

10. A compound according to claim 1, wherein A is C—X$_1$.

11. A compound according to claim 1, wherein D is C—X$_2$.

12. A compound according to claim 1, wherein E is C—X$_3$.

13. A compound according to claim 1, wherein G is C—X$_4$.

14. A compound according to claim 1, wherein J is C—X$_1$.

15. A compound according to claim 1, wherein L is O or NH.

16. A compound according to claim 1, wherein M is C—$X_2$.

17. A compound according to claim 1, wherein one of A, D, E, and G is N.

18. A compound according to claim 1, which is thioisobutyric acid S-(3-{[1-(2-ethyl-butyl)-cyclohexane-carbonyl]-amino}-naphthalen-2-yl) ester.

19. A compound according to claim 1, which is 1-methyl-cyclohexanecarboxylic acid(2-mercapto-naphthalen-1-yl)-amide.

20. A pharmaceutical composition comprising a compound according to claim 1 and a pharmaceutically acceptable carrier.

* * * * *